US012569161B2

(12) United States Patent
Schulman et al.

(10) Patent No.: US 12,569,161 B2
(45) Date of Patent: Mar. 10, 2026

(54) METHODS FOR LONG-DISTANCE RESPIRATION RATE MEASUREMENT USING NOISY AND IRREGULARLY SAMPLED SENSOR SIGNALS

(71) Applicant: KONINKLIJKE PHILIPS N.V., Eindhoven (NL)

(72) Inventors: Daniel Jason Schulman, Cambridge, MA (US); Ikaro Garcia Araujo da Silva, Cambridge, MA (US); Sara Mariani, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 295 days.

(21) Appl. No.: 18/510,878

(22) Filed: Nov. 16, 2023

(65) Prior Publication Data

US 2024/0172959 A1 May 30, 2024

Related U.S. Application Data

(60) Provisional application No. 63/428,556, filed on Nov. 29, 2022.

(51) Int. Cl.
*A61B 5/00* (2006.01)
*A61B 5/08* (2006.01)

(52) U.S. Cl.
CPC .......... *A61B 5/0816* (2013.01); *A61B 5/0062* (2013.01); *A61B 5/0803* (2013.01);
(Continued)

(58) Field of Classification Search
CPC ... A61B 5/0816; A61B 5/0062; A61B 5/0803; A61B 5/7235; A61B 5/742; A61B 2562/02; A61B 5/7253; G16H 50/30
See application file for complete search history.

(56) References Cited

U.S. PATENT DOCUMENTS

| | | | |
|---|---|---|---|
| 8,454,528 | B2 | 6/2013 | Yuen |
| 9,265,456 | B2 | 2/2016 | Kirenko |
| 11,185,289 | B2 | 11/2021 | Tarsaud |

FOREIGN PATENT DOCUMENTS

| | | |
|---|---|---|
| CN | 111568417 B | 8/2020 |
| CN | 114617544 A | 6/2022 |

(Continued)

OTHER PUBLICATIONS https://www.usa.philips.com/a-w/about/news/archive/standard/news/press/2019/20191022-philips-and-the-us-department-of-defense-develop-breakthrough-technology-using-ai-to-identify-infection-more-than-48-hours-before-observable-symptoms.html.

(Continued)

*Primary Examiner* — Scott M. Getzow

(57) ABSTRACT

A system for measuring long-distance respiration rate is provided. The system includes a processing unit configured to receive and normalized a sensor output signal. The processing unit is further configured to compute a series of four Discrete Prolate Spheroid window functions. For each of the series of four Discrete Prolate Spheroid window functions, the processing unit is configured to (1) multiply the normalized sensor output signal by the Discrete Prolate Spheroid window function to produce a windowed output signal, and (2) compute a Lomb-Scargle periodogram based on the windowed output signal. The processing unit is further configured to compute a weighted average of the Lomb-Scargle periodograms to produce an averaged periodogram. The processing unit is further configured to compute a frequency corresponding to a peak estimated spectral density on the averaged periodogram. The processing unit is further configured to output breaths per minute data based on the frequency.

15 Claims, 16 Drawing Sheets

(52) U.S. Cl.
    CPC ............ *A61B 5/7235* (2013.01); *A61B 5/742*
                   (2013.01); *A61B 2562/02* (2013.01)

(56) References Cited

FOREIGN PATENT DOCUMENTS

| | | |
|---|---|---|
| JP | 2018187090 A | 11/2018 |
| WO | 2023068373 A1 | 4/2023 |

OTHER PUBLICATIONS

Feng, T. et al., "610: Predicting Infection Type Upon Clinical Suspicion of Hospital-Acquired Infection." Critical Care Medicine, (2020) Abstract.
https://www.defenseone.com/technology/2020/09/militarys-latest-wearables-can-detect-illness-two-days-you-get-sick/168664/.

Conroy, B. et al., "Real-time infection prediction with wearable physiological monitoring and AI: Aiding military workforce readiness during COVID-19." Scientific Reports (2022) 12:3797.
https://mhealthintelligence.com/news/philips-defense-department-expand-mhealth-project-for-infection-tracking.
Zeng, T. et al., "Automated determination of wakefulness and sleep in rats based on non-invasively acquired measures of movement and respiratory activity", Journal of Neuroscience Methods, Elsevier, Amsterdam, NL, vol. 204, No. 2, (Dec. 1, 2011).
Thomson, D.J., "Spectrum estimation and harmonic analysis", Proceedings of the IEEE, vol. 70, No. 9, (Jan. 1, 1982), pp. 1055-1096.
Nasan, K. et al., "Analysis of Spectral Estimation Algorithms for Accurate Heart Rate and Respiration Rate Estimation Using an Ultra-Wideband Radar Sensor", IEEE Reviews in Biomedical Engineering, IEEE, USA, vol. 17, (Oct. 6, 2022), pp. 297-309.
Chen, W. et al., "Estimating Carotid Pulse and Breathing Rate from Near-infrared Video of the Neck", Arxiv. org, Cornell University Library, Ithaca, NY, (May 24, 2018).

918 —— receiving a plurality of sensor output signals

920 —— computing a plurality of periodograms
corresponding to the plurality of sensor output signals 922 —— computing the frequency corresponding to the peak spectral
estimate density of an average of the plurality of periodograms

METHODS FOR LONG-DISTANCE RESPIRATION RATE MEASUREMENT USING NOISY AND IRREGULARLY SAMPLED SENSOR SIGNALS

CROSS-REFERENCE TO RELATED APPLICATIONS

This application claims priority to U.S. Provisional Patent Application Ser. No. 63/428,556, filed on Nov. 29, 2022, and titled "Methods for Long-Distance Respiration Rate Measurement Using Noisy and Irregularly Sampled Sensor Signals," which application is herein incorporated by reference in its entirety.

GOVERNMENT LICENSE RIGHTS

This invention was made with government support under Grant No. HDTRA12110017 (MESH) awarded by the United States Department of Defense. The government has certain rights to this invention.

FIELD OF THE DISCLOSURE

The disclosed subject matter generally pertains to long-distance contactless estimation of respiration rate.

BACKGROUND

Changes in respiratory rate are meaningful indicators of inflammation and infection. Long distance contactless monitoring of respiration rates for infection surveillance is desirable in scenarios where wearable sensors or short-distance measurement (e.g., in a fixed-location kiosk setting) are impractical, including battlefields, disaster areas, emergency rooms, and staff monitoring.

SUMMARY OF THE DISCLOSURE

The present disclosure is directed to a system that can yield more reliable respiration rate estimates from noisy signals with infrequent and irregular sampling. Building on these methods, this disclosure describes a system for long-distance respiration rate measurement with one or more low-cost sensing methods.

Generally, in one aspect, a system for measuring long-distance respiration rate is provided. The system includes a processing unit configured to receive a sensor output signal.

The processing unit is further configured to normalize the sensor output signal.

The processing unit is further configured to compute a series of four Discrete Prolate Spheroid window functions. For each of the series of four Discrete Prolate Spheroid window functions, the processing unit is configured to (1) multiply the normalized sensor output signal by the Discrete Prolate Spheroid window function to produce a windowed output signal, and (2) compute a Lomb-Scargle periodogram based on the windowed output signal.

The processing unit is further configured to compute a weighted average of the Lomb-Scargle periodograms to produce an averaged periodogram.

The processing unit is further configured to compute a frequency corresponding to a peak estimated spectral density on the averaged periodogram.

The processing unit is further configured to output breaths per minute data based on the frequency.

According to an example, the system further includes a plurality of sensors. The plurality of sensors are configured to measure a chest position of an individual. The plurality of sensors are further configured to provide a plurality of sensor output signals. The processing unit is further configured to (1) compute a plurality of periodograms corresponding to the plurality of sensor output signals, and (2) compute the frequency corresponding to the peak spectral estimate density of an average of the plurality of periodograms.

According to an example, the Lomb-Scargle periodogram is computed using a sequence of frequencies ranging from 4 to 50 breaths per minute.

According to an example, the Lomb-Scargle periodogram is spaced at 0.01 breaths per minute.

According to an example, each of the series of the Discrete Prolate Spheroid window functions is computed using a bandwidth of 8 seconds.

According to an example, the system further includes a display unit configured to (1) receive the breaths per minute data and (2) display the breaths per minute data.

According to an example, the processing unit is configured to normalize the sensor output signal to have a mean of 0 and a standard deviation of 1.

According to an example, eigenvalues of the series of four Discrete Prolate Spheroid window functions are used as weights to compute the weighted average.

According to an example, the system of claim 1 further includes a sensor configured to measure a chest position of an individual and provide the sensor output signal based on the chest position of the individual. The sensor may be an RGB camera or a laser rangefinder.

Generally, in another aspect, a method of measuring long-distance respiration rate is provided. The method includes receiving a sensor output signal of an individual's chest position.

The method further includes normalizing the sensor output signal.

The method further includes computing a series of four Discrete Prolate Spheroid window functions. For each of the series of four Discrete Prolate Spheroid window functions, the method further includes multiplying the normalized sensor output signal by the Discrete Prolate Spheroid window function to produce a windowed output signal, and computing a Lomb-Scargle periodogram based on the windowed output signal.

The method further includes computing a weighted average of the Lomb-Scargle periodograms to produce an averaged periodogram.

The method further includes computing a frequency corresponding to a peak estimated spectral density on the averaged periodogram.

The method further includes outputting breaths per minute data based on the frequency.

According to an example, each of the series of the Discrete Prolate Spheroid window functions is computed using a bandwidth of 8 seconds. Further, eigenvalues of the series of four Discrete Prolate Spheroid window functions are used as weights to compute the weighted average.

According to an example, the Lomb-Scargle periodogram is computed using a sequence of frequencies ranging from 4 to 50 breaths per minute. Further, the Lomb-Scargle periodogram is spaced at 0.01 breaths per minute.

According to an example, the method further includes (1) receiving a plurality of sensor output signals, (2) computing a plurality of periodograms corresponding to the plurality of sensor output signals; and (3) computing the frequency corresponding to the peak spectral estimate density of an average of the plurality of periodograms.

According to an example, the sensor output signal is normalized to have a mean of 0 and a standard deviation of 1.

Generally, in another aspect, a non-transitory computer readable storage medium embodied thereon a program executable by a processor for performing a method for measuring long distance respiration rate is provided. The method includes receiving a sensor output signal of an individual's chest position.

The method further includes normalizing the sensor output signal.

The method further includes computing a series of four Discrete Prolate Spheroid window functions. For each of the series of four Discrete Prolate Spheroid window functions, the method further includes multiplying the normalized sensor output signal by the Discrete Prolate Spheroid window function to produce a windowed output signal, and computing a Lomb-Scargle periodogram based on the windowed output signal.

The method further includes computing a weighted average of the Lomb-Scargle periodograms to produce an averaged periodogram.

The method further includes computing a frequency corresponding to a peak estimated spectral density on the averaged periodogram.

In various implementations, a processor or controller may be associated with one or more storage media (generically referred to herein as "memory," e.g., volatile and non-volatile computer memory such as RAM, PROM, EPROM, EEPROM, floppy disks, compact disks, optical disks, magnetic tape, SSD, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects as discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

Figure 1:
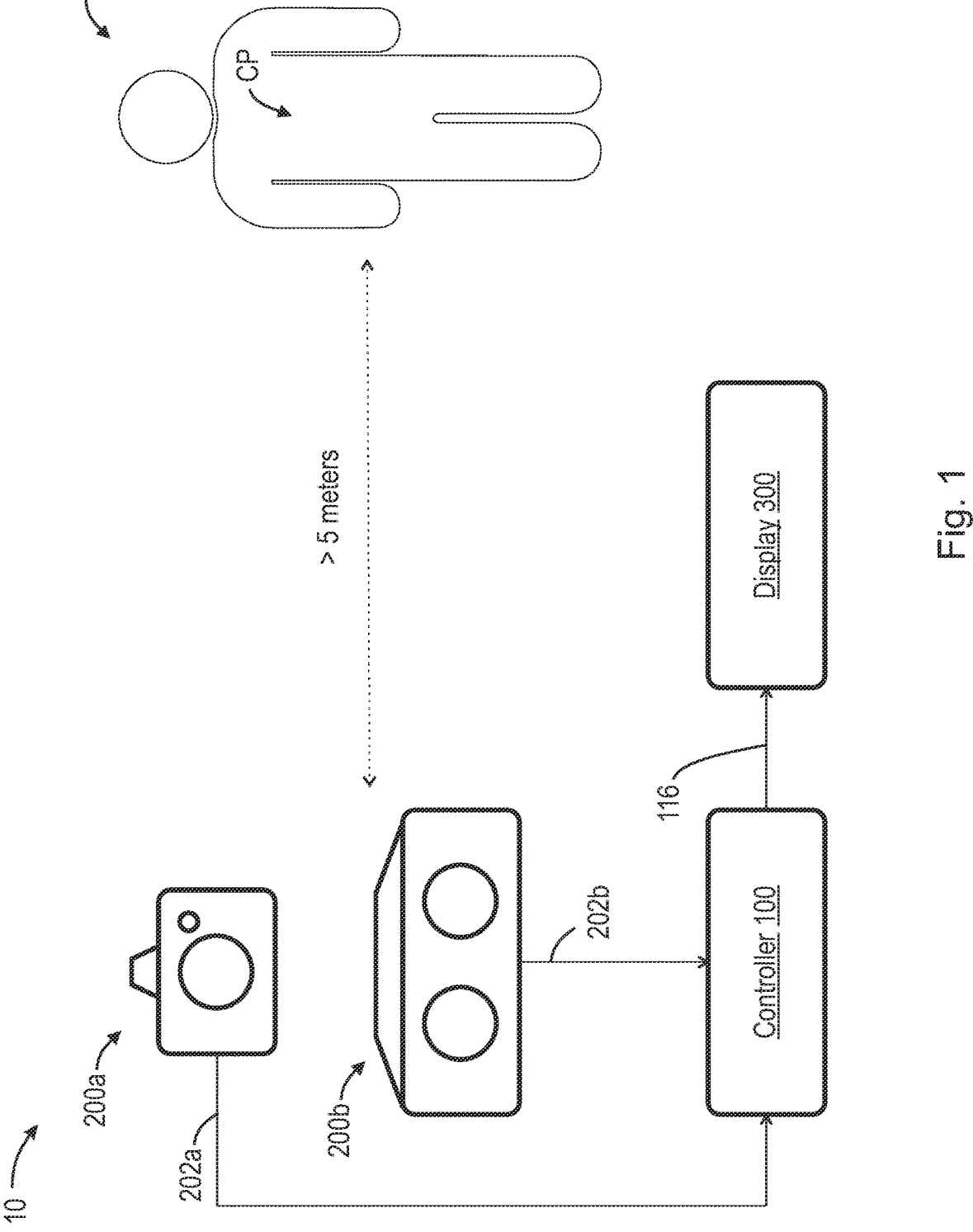
FIG. 1 is an illustration of a system for long-distance respiration rate measurement, in accordance with an example.

The present disclosure is directed to a system that can yield more reliable respiration rate estimates from noisy signals with infrequent and irregular sampling. Building on these methods, this disclosure describes a system for long-distance respiration rate measurement with one or more low-cost sensing methods.

The disclosed subject matter generally pertains to long-distance and contactless estimation of respiration rate. Respiration rates can be estimated from repeated measurements of the movement of an individual's chest, or, equivalently, the distance of the chest from a sensor. Using currently known methods, this can yield poor estimates at long distances, when many sensors produce measurements that are noisy, have low sampling rates, and are irregularly sampled in time. Efficient algorithms have been developed for the early prediction of infection based on laboratory values and vital signs. Specific biomarkers have been identified as most predictive of infection. Respiratory rate is one of the top predictors of infection.

Further development has transferred these algorithms to the out-of-hospital context, where laboratory data were typically not available, and the input to the model consisted of time series data from wearable devices. This disclosure focuses on allowing monitoring of respiratory without the burden of wearable devices and at substantial distances from the subject. This approach is particularly suited for situations in which it is inconvenient for the subject to wear a wristband, patch, or chest strap, like in military applications where sensors can be a burden to operations. In some examples, the monitored respiratory rate may then be used as part of an infection prediction.

There are multiple sensing modalities that have been used to estimate a respiration rate from chest movement via repeated measurements of distance from a sensor to the subject's chest. An advantage of this approach is that these sensing methods are widely available, often as inexpensive commercial off-the-shelf (COTS) hardware. In this disclosure, embodiments incorporating cameras and laser rangefinders are disclosed, but embodiments may use other sensing devices and methods as well.

In conventional systems, these sensing modalities have been used in controlled conditions and at short distances from the subject. In this disclosure, systems and methods are provided to enable using these sensing modalities at long distances and in varying environmental conditions. The systems and methods implement signal processing methods that have not been previously applied to physiological signal measurement, to infection surveillance, or to any of the other topics relevant to this disclosure.

There are a set of well-understood algorithmic methods that have been applied in this application domain for detecting a frequency (in this case, a respiration rate) from a sampled signal over time (in this case, the distance from the sensor to a subject's chest). These methods have been effective in the scenarios for which they were designed, which typically include a sensor at short distances to a subject (e.g., in the same room, at a distance of less than 5 meters), and in environments (e.g., a physician's office) where lighting, ambient noise, occluding objects, and similar factors can be controlled.

These sensing modalities have not previously been applied at long distances or in settings where environmental difficulties may be present. The present disclosure considers both indoor and outdoor environments. At outdoor environments, changes in lighting are more likely to occur, and visual occlusion by rain, smoke, or fog may occlude laser rangefinder or camera-based sensors. As distances increase, and environmental factors are present, the quality of sensor signals degrades in several ways, including additional noise and variability, lower sampling rate, and irregular sampling in time, including missing samples (e.g., if visual occlusion causes a sensor to momentarily fail to produce a measurement) and variation in the period between samples.

The present disclosure addresses the last issue, that of irregular sampling. Typical methods of frequency estimation (e.g., Fourier transform) assume samples are regularly spaced in time, and require interpolation to a regular grid to be applied to irregularly sampled data. In turn, interpolation may confound the estimation by introducing noise and false frequency components in the signal.

The disclosed systems and methods are based on a new insight, that a set of methods developed in other application domains (estimation of light curves of distant objects in astrophysics) can be adapted to respiration rate estimation in these conditions. These methods include a Lomb-Scargle periodogram, a method of estimating spectral density of an irregularly sampled signal, and a Thompson multitaper smoothing method, which reduces noise in spectral density estimates. Application of a Lomb-Scargle periodogram to analysis of ECG and other physiological signals has not previously been applied to long-distance respiration rate estimation, and has not been applied in combination to respiration rate estimation.

To implement these systems and methods, the minimal set of elements needed is (1) one or more sensors and (2) a computer system. The one or more sensors and associated components deliver repeated measurements of an individual's chest position, at variable distance and in varying environmental conditions. The one or more sensors may include a red-green-blue wavelength (RGB) camera or a laser rangefinder. A commercial off-the-shelf RGB camera (such as a Sony DSC-RX10 or Nikon COOLPIX P1000) may be paired with a computer vision system capable of estimating chest position from an image according to methods developed as part of the contactless monitoring system described in U.S. Pat. No. 9,265,456 titled "DEVICE AND METHOD FOR DETERMINING VITAL SIGNS OF A SUBJECT". The commercial, off-the-shelf laser rangefinders are configured to measure distances with high frame rate, and to transmit the measurements to a computer. In some examples, the laser rangefinder could be a Leica DISTO D810 or a Bosch GLM400CL. Further, the computer system may be configured for software implementation of the algorithms described in this disclosure. In some examples, the systems and methods may be in communication with a system that uses the remotely measured respiration rate to provide health assessments of the individual being monitored. There is no on-market or in development solution or device for the measurement of vital signs at long distances.

Estimation of a respiration rate in breaths per minute can be accomplished via the following steps. First, the computer system normalizes the sensor signal to have a mean of zero and a standard deviation of one.

Second, the computer system computes the first four Discrete Prolate Spheroid window functions, following standard formulas, using a bandwidth of 8 seconds. As these window functions are typically defined for a regularly sampled signal, cubic interpolation may be used to generate the window function for an irregularly sampled signal.

Third, and separately for each window function, the computer system (a) multiplies the sensor signal by the window function and (b) computes a Lomb-Scargle periodogram using a sequence of frequencies ranging from 4 to 50 breaths per minute, and spaced at 0.01 breaths per minute.

Fourth, the computer system computes a weighted average of the periodograms produced in the previous step, using the eigenvalues of the window functions as weights.

Optionally, if multiple sensor signals are available (e.g., from multiple sensors), periodograms may be computed separately for each signal (following steps 1-4) and combined via averaging or other methods.

Fifth, the computer system computes the estimated breaths per minute as the frequency corresponding to the peak estimated spectral density on the final averaged periodogram.

Note that different parameters of the method may be chosen to adapt to particular sensors or applications, or to select a different trade-off between computational needs and performance. These parameters may include: the number of window functions used (step 2); the bandwidth of the window functions (step 2); the range of frequencies used to compute the Lomb-Scargle periodograms (step 3b); and the resolution (spacing) of frequencies examined (step 3b).

As discussed previously, aspects of this disclosure may be applied in a number of ways. For instance, aspects may be used to monitor warfighters at potential risk of infection, which is important to (1) ensure their optimal performance in military operations and (2) prevent spread of pathogens in close-contact living. Additionally, aspects may be used to monitor high-risk people in community living, e.g., elderly patients in a retirement home, or people in constrained quarters such as inmates, ship crew, and medical staff. Other applications of long-distance monitoring of respiration rate are possible.

Turning now to the figures, FIG. 1 illustrates a non-limiting example of a system 10 for long-distance measurement of respiration rate. As shown in FIG. 1, the system 10 generally includes a controller 100, one or more sensors 200a, 200b, and a display 300. As will be shown in more detail in FIGS. 2, 3, and 10, the controller 100 includes a processor 125, a memory 175, and a transceiver 185. In some examples, the processor 125 may be embodied as a plurality of processing units. Similarly, the memory 175 may be embodied as a plurality of memory storage units. The transceiver 185 may be used to enable wireless communication between the controller 100 and the other aspects of the system 10, such as the sensors 200a, 200b and/or the display 300.

The example system 10 of FIG. 1 further includes a first sensor 200a embodied as an RGB camera and a second sensor 200b embodied as a laser rangefinder. Generally, the sensors 200a, 200b may be any device capable of visually capturing data reflective of chest position CP of an individual I arranged at a long-distance from the sensors 200a, 200b. In some examples, the distance between the sensors 200a, 200b and the individual I is at least five meters. In some examples, the system 10 only includes a single sensor 200. In other examples, the system 10 may include more than two sensors. In even further examples, the system 10 may include two or more sensors of the same type, such as two or more RGB cameras or laser rangefinders.

The first sensor 200a is configured to transmit, via wired or wireless connection, a first output sensor signal 202a to the controller 100. Similarly, the second sensor 200b is configured to transmit, via wired or wireless connection, a second output sensor signal 202b to the controller 100. The controller 100 processes the first and second output signals 202a, 202b to estimate breath per minute data 116 corresponding to the respiration rate of the individual I. In some examples, the controller 100 is arranged proximate to the sensors 200a, 200b. In other examples, the controller 100 may be arranged a significant distance from the sensors 200a, 200b, requiring data to be transferred from the sensors 200a, 200b to the controller 100 via cloud computing.

The example system 10 of FIG. 1 further includes a display 300. In some examples, the display 300 may be incorporated in the controller 100. In other examples, the display 300 could be incorporated into a discrete device, such as a smartphone or a personal computer. The display 300 is configured to receive, via wired or wireless connection, the estimated breath per minute data 116. The display 300 is then configured to show the estimated breath per minute data 116 on a display screen, such as a touch screen.

Figure 2:
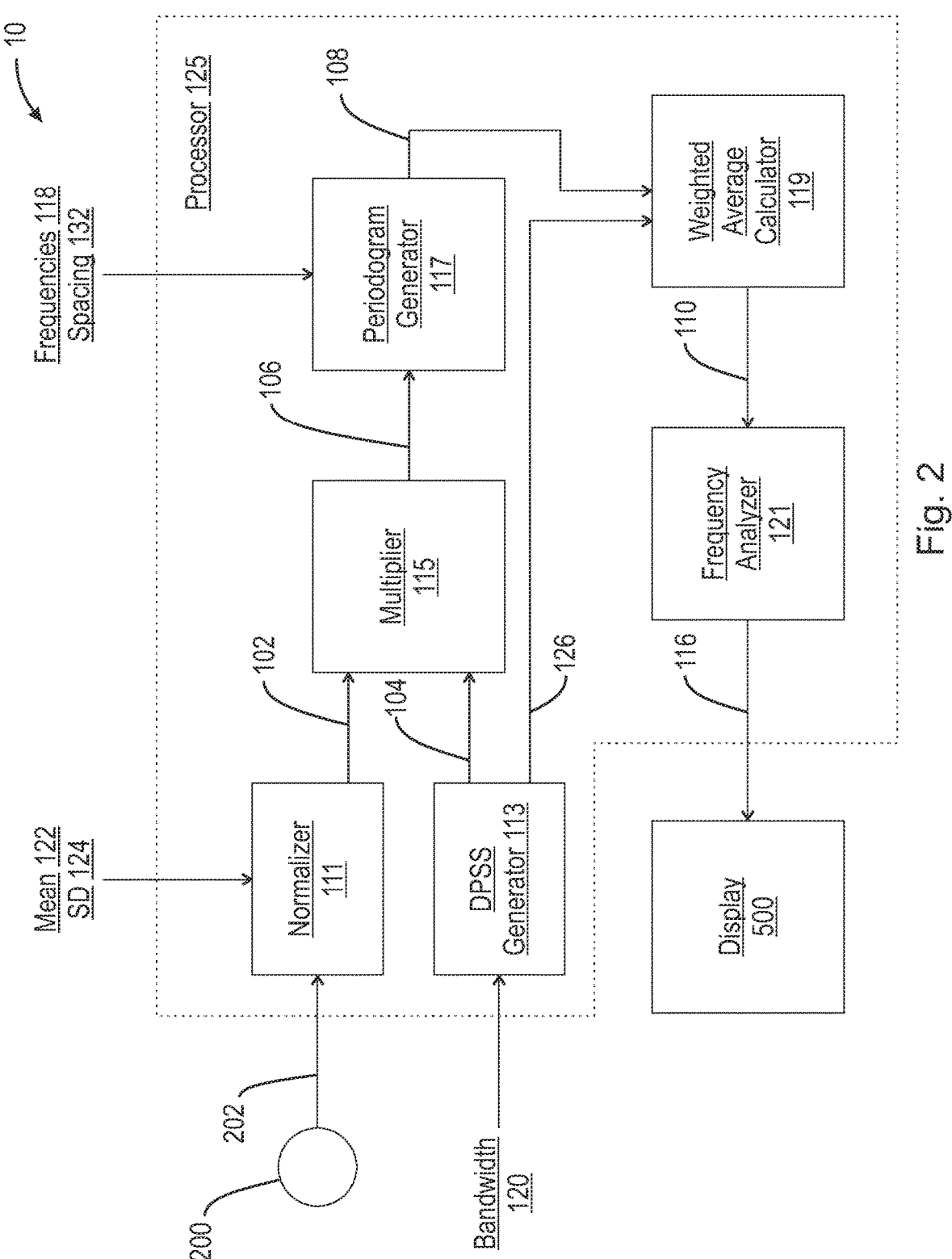
FIG. 2 is a block diagram of a system for long-distance respiration rate measurement, in accordance with an example.
Figure 4A:
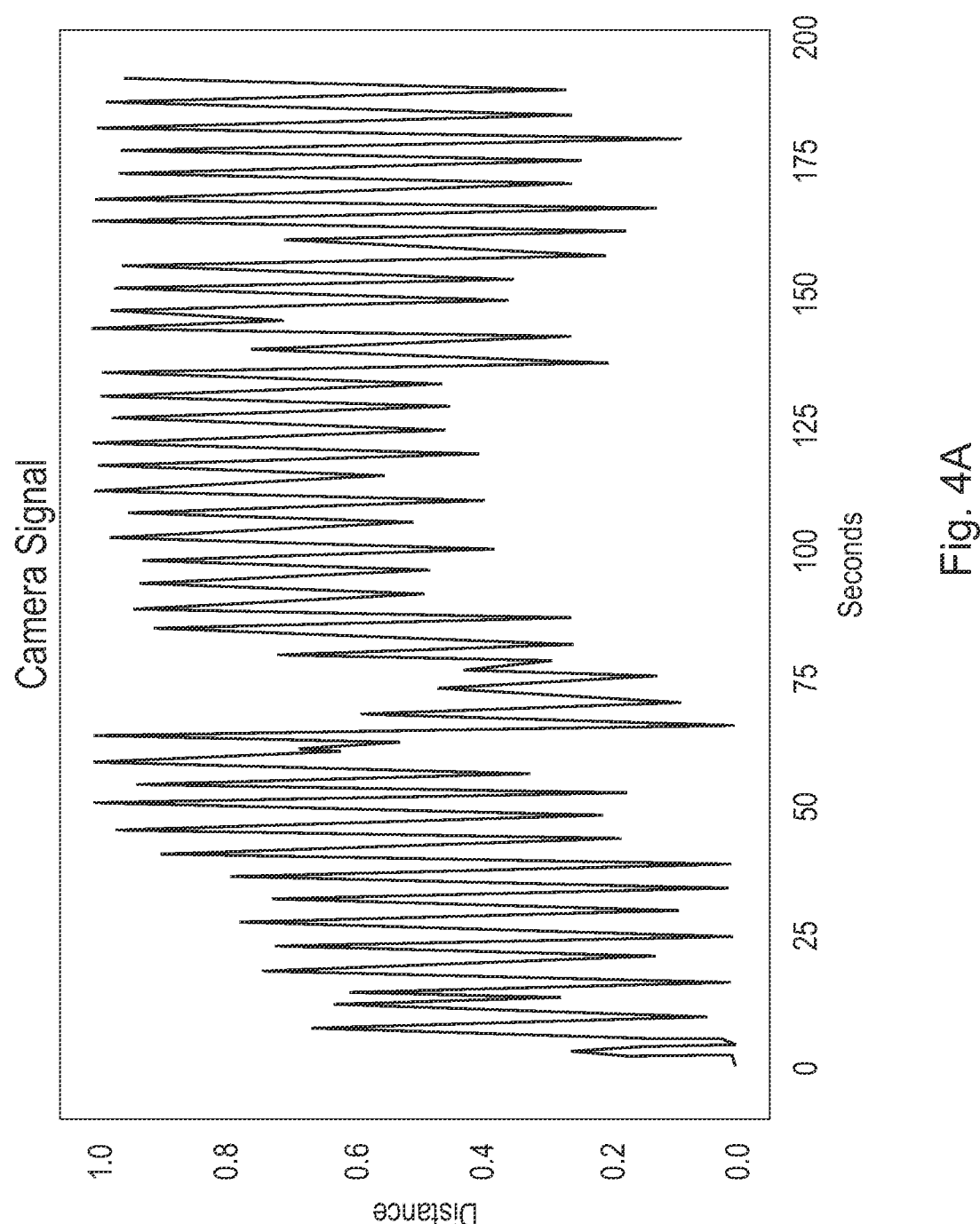
FIG. 4A is a time domain plot of data captured by a camera, in accordance with an example.
Figure 4B:
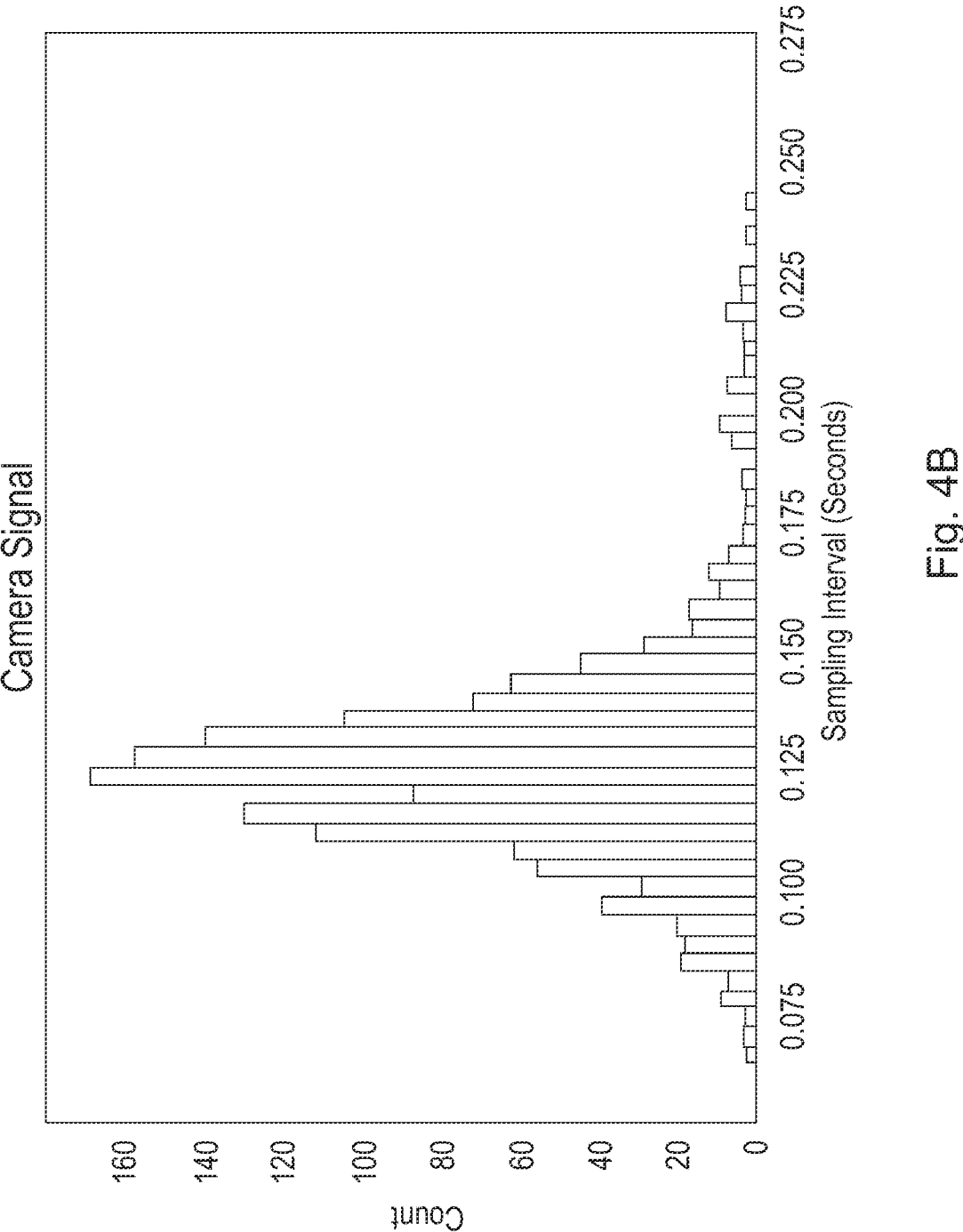
FIG. 4B is a histogram of data captured by a camera, in accordance with an example.
Figure 5A:
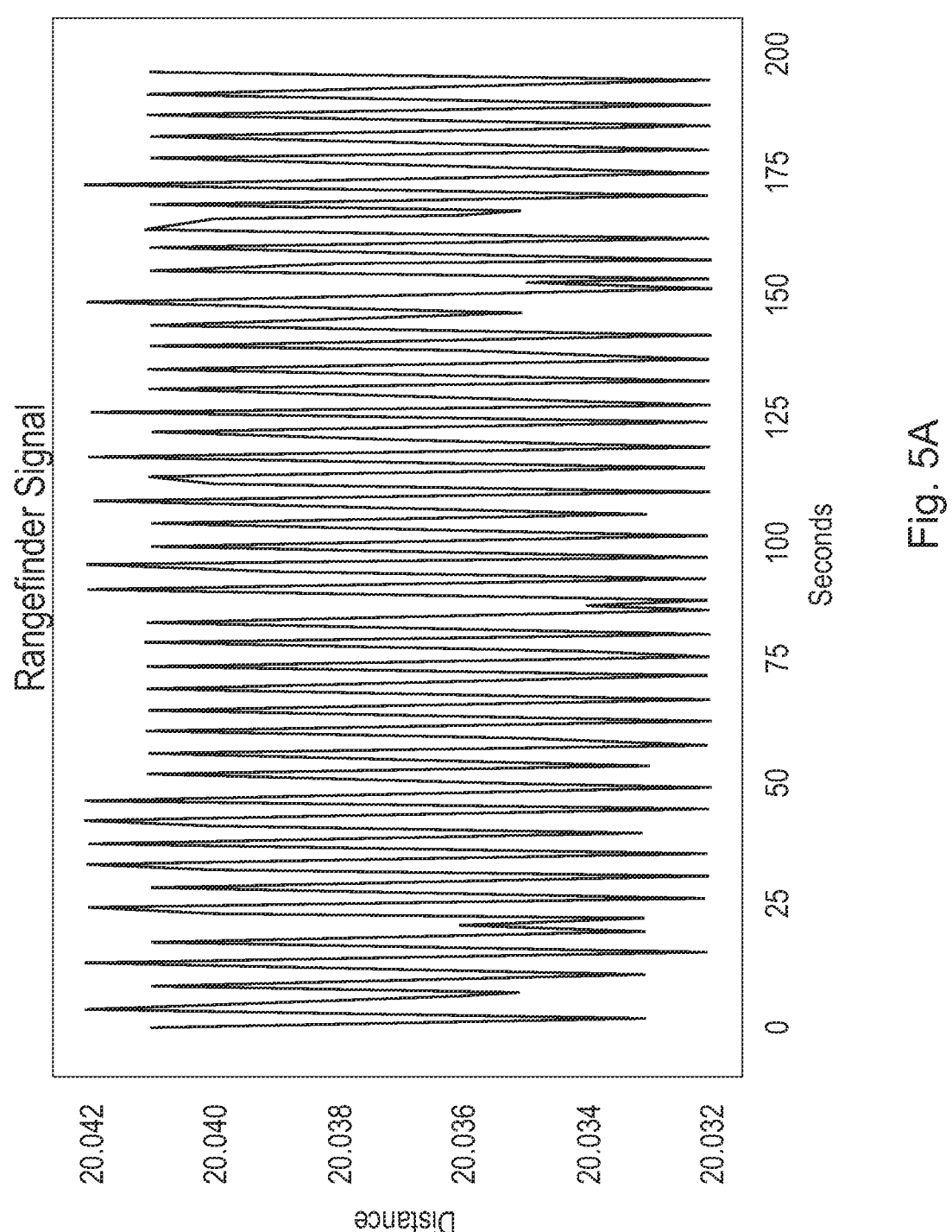
FIG. 5A is a time domain plot of data captured by a rangefinder, in accordance with an example.
Figure 5B:
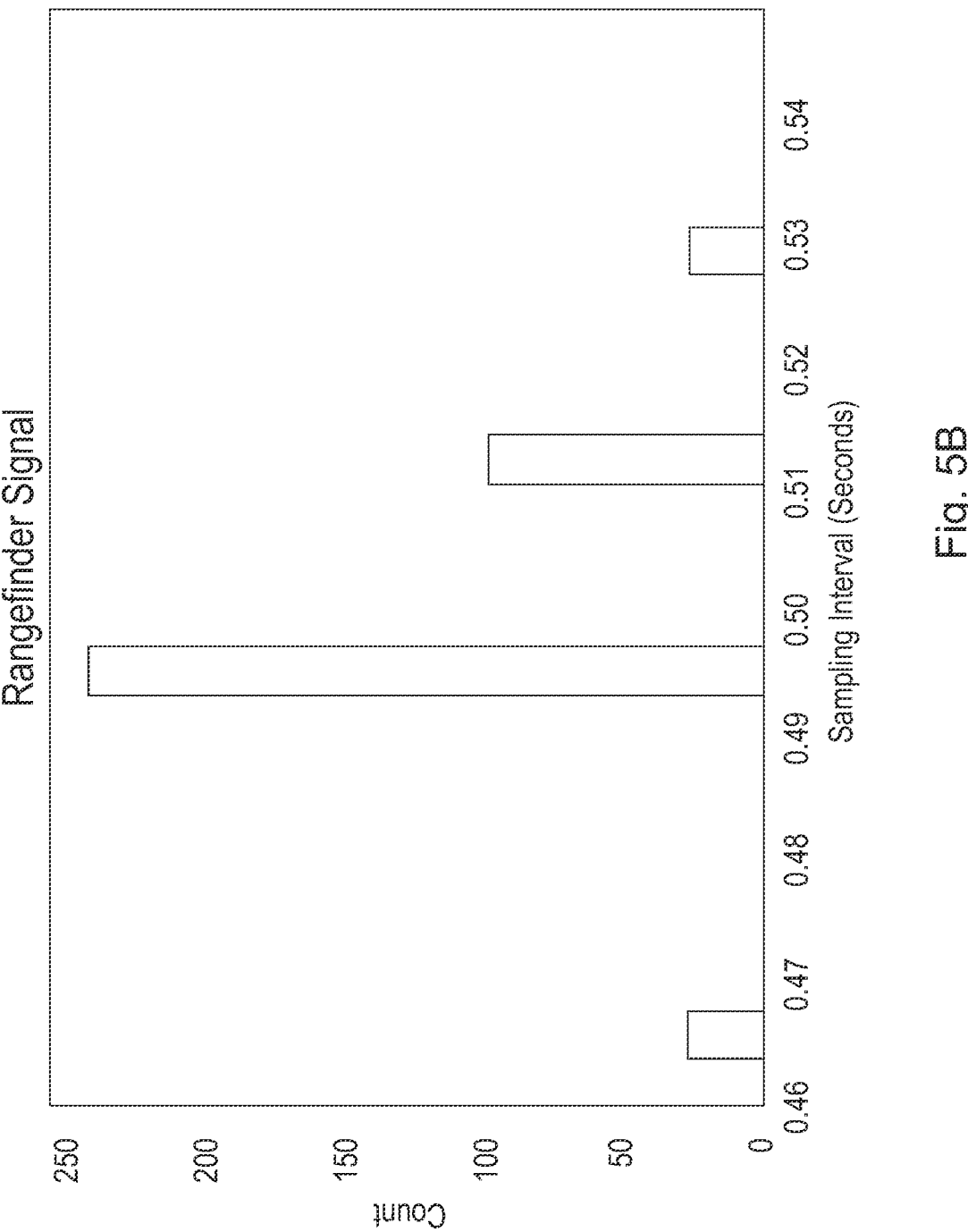
FIG. 5B is a histogram of data captured by a rangefinder, in accordance with an example.

FIG. 2 illustrates a block diagram illustrating the data processing of a sensor output signal 202 to breath per minute data 116. As shown in the non-limiting example of FIG. 2, a sensor 200 (such as an RGB camera or a laser rangefinder) provides the sensor output signal 202 to the processor 125. An example of a time domain sensor output signal 202 provided by a camera is shown in FIG. 4A. A histogram of the sensor output signal 202 provided by the camera is shown in FIG. 4B illustrating the sampling irregularity of the sensor output signal 202. In another example, a time domain sensor output signal 202 provided by a rangefinder is shown in FIG. 5A. A histogram of the sensor output signal 202 provided by the rangefinder is shown in FIG. 5B illustrating the sampling irregularity of the sensor output signal 202. In the example of the system 10 of FIG. 2, the sensor output signal 202 may correspond to an RGB camera, a rangefinder, or another device for capturing chest position CP of an individual I.

The sensor output signal 202 is then provided to normalizer 111 to generate a normalized sensor output signal 102. The normalized sensor output signal 102 is normalized according to values of a mean 122 and a standard deviation 124 stored in the memory 175 of the controller 100. In a preferred example, the normalized sensor output signal 102 is normalized according to a mean 122 of zero and a standard deviation 124 of one.

Figure 6:
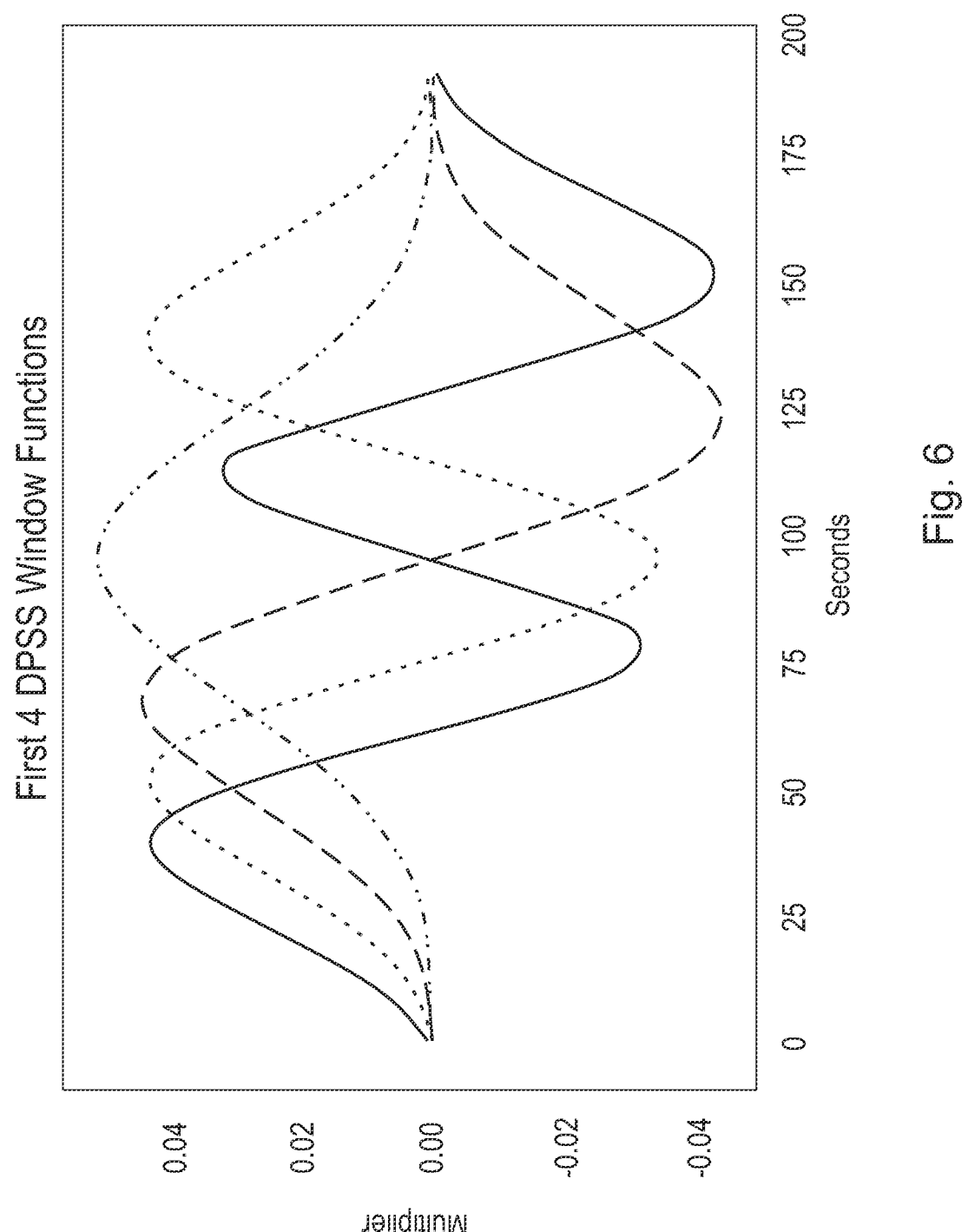
FIG. 6 is an example of a series of four discrete prolate spheroid sequence window functions, in accordance with an example.

The processor 125 further includes a Discrete Prolate Spheroid Sequence (DPSS) generator 113 configured to generate a series of four DPSS window functions 104. Examples of the four DPSS window functions 104 are shown in FIG. 6. The DPSS window functions 104 may be generated according to a bandwidth 120 stored in the memory 175 of the controller 100. In a preferred example, the value of the bandwidth 120 is eight seconds.

The processor 125 further includes a multiplier 115 to multiply the normalized sensor output signal 102 with each of the four DPSS window functions 104 to produce four windowed output signals 106. These four windowed output signals 106 are then provided to a Lomb-Scargle periodogram generator 117. The periodogram generator 117 generates a series of Lomb-Scargle periodograms 108, one for each of the four windowed output signals 106. The periodograms are generated based on a sequence of frequency values 118 and a spacing value 132. The sequence of frequencies 118 may range from four to fifty breaths per minute. The spacing 132 of the periodograms 108 may be set to be 0.01 breaths per minute.

Figure 7A:
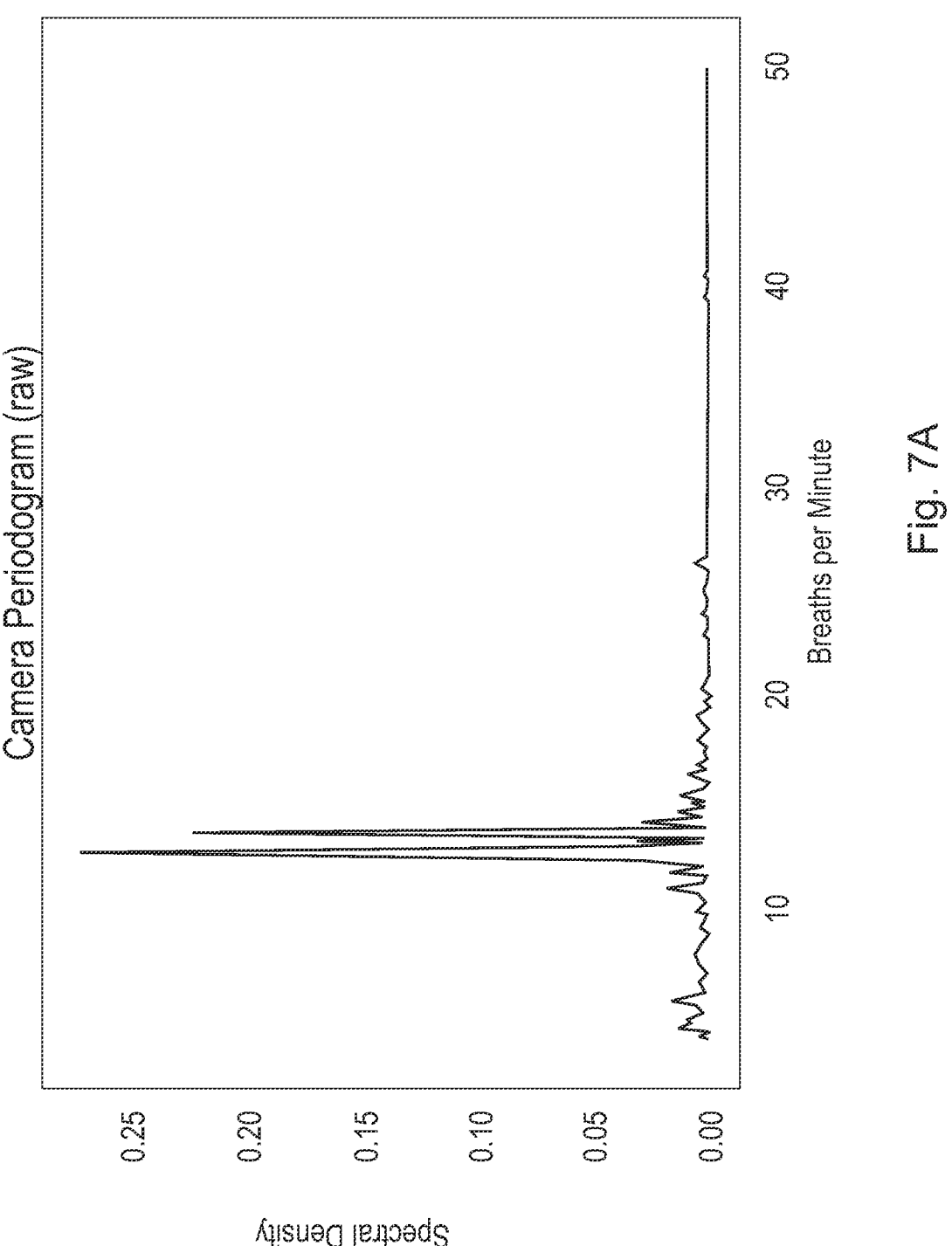
FIG. 7A is an example raw periodogram based on data captured by a camera, in accordance with an example.
Figure 7B:
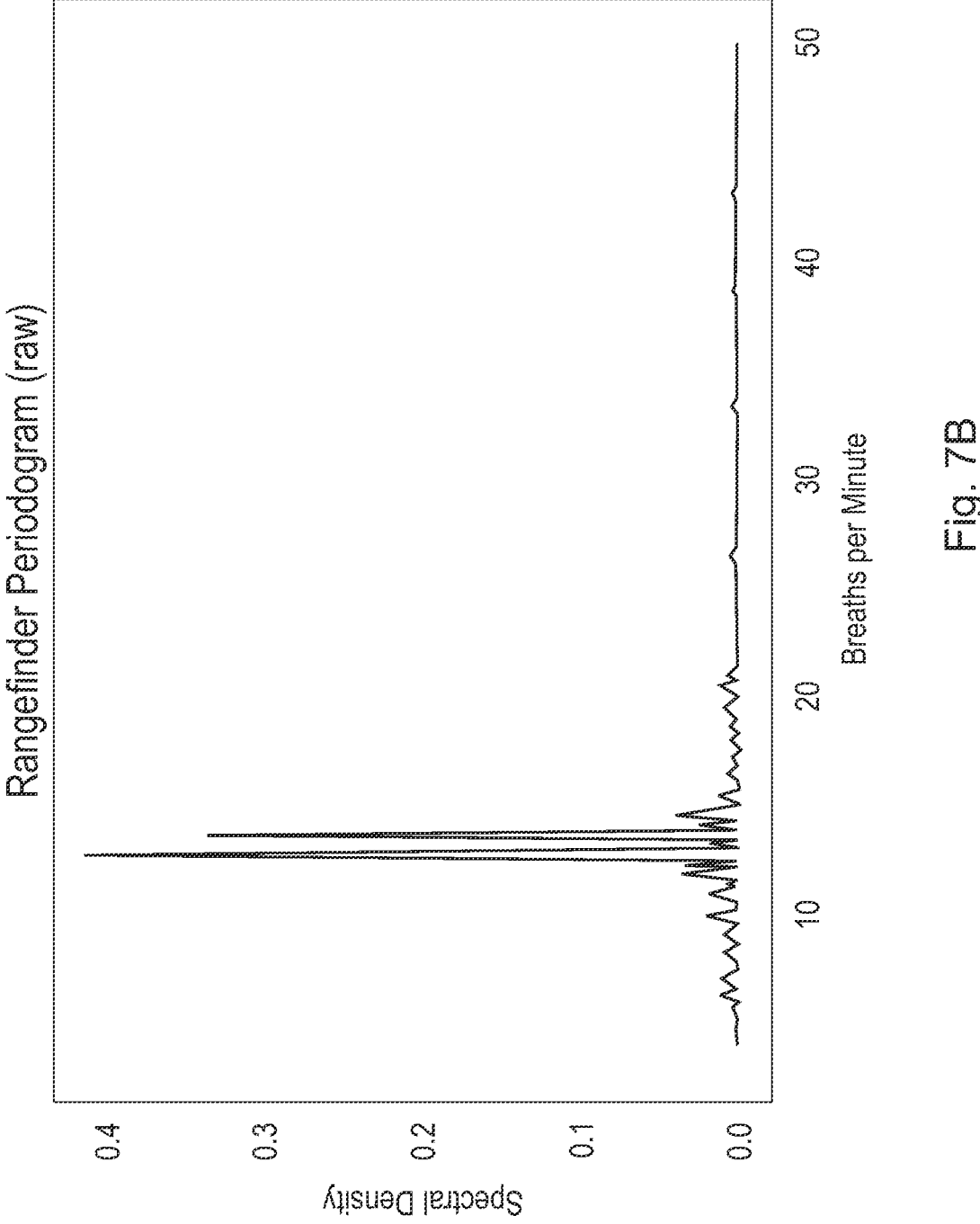
FIG. 7B is an example raw periodogram based on data captured by a rangefinder, in accordance with an example.
Figure 8A:
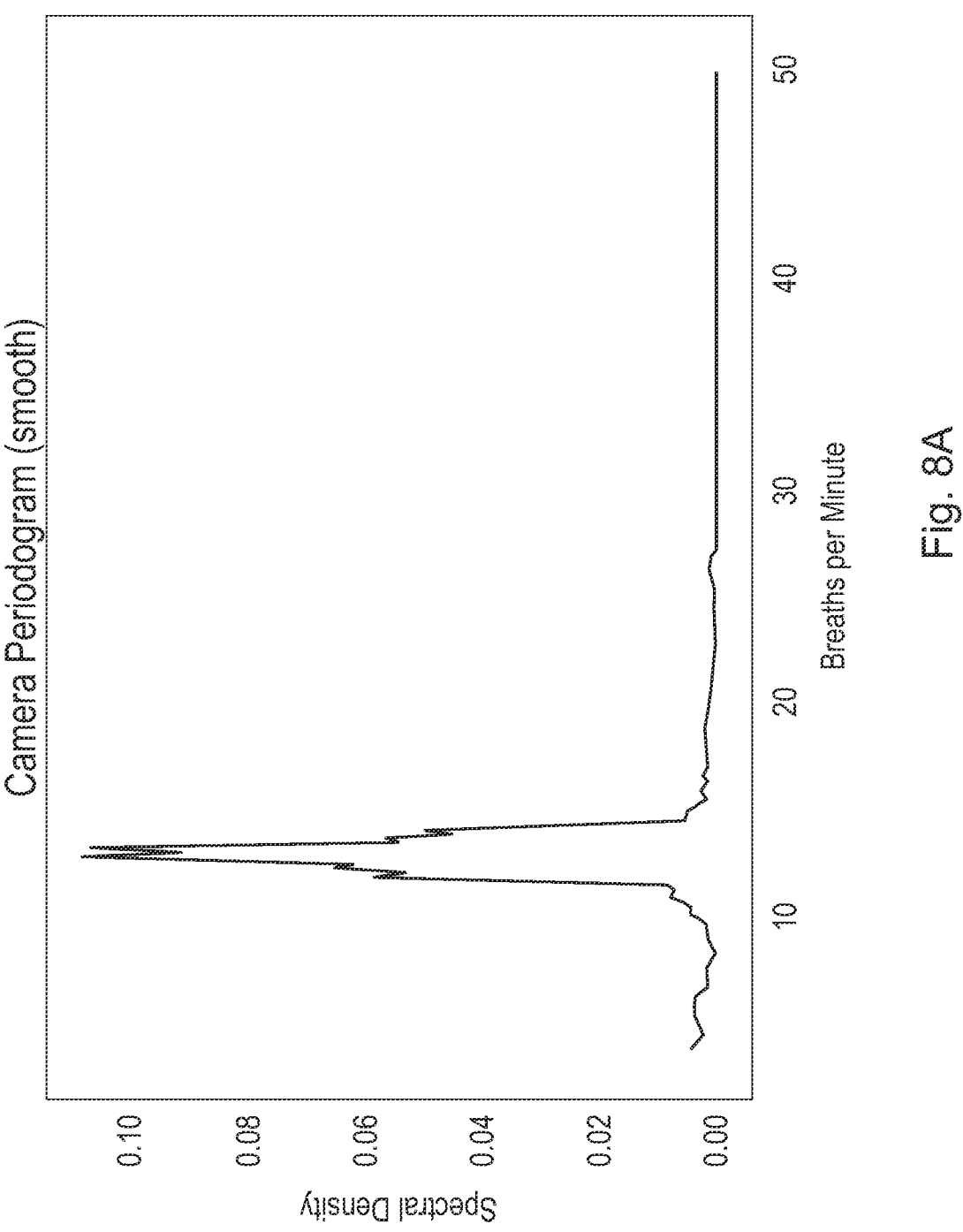
FIG. 8A is an example smoothed periodogram based on data captured by a camera, in accordance with an example.
Figure 8B:
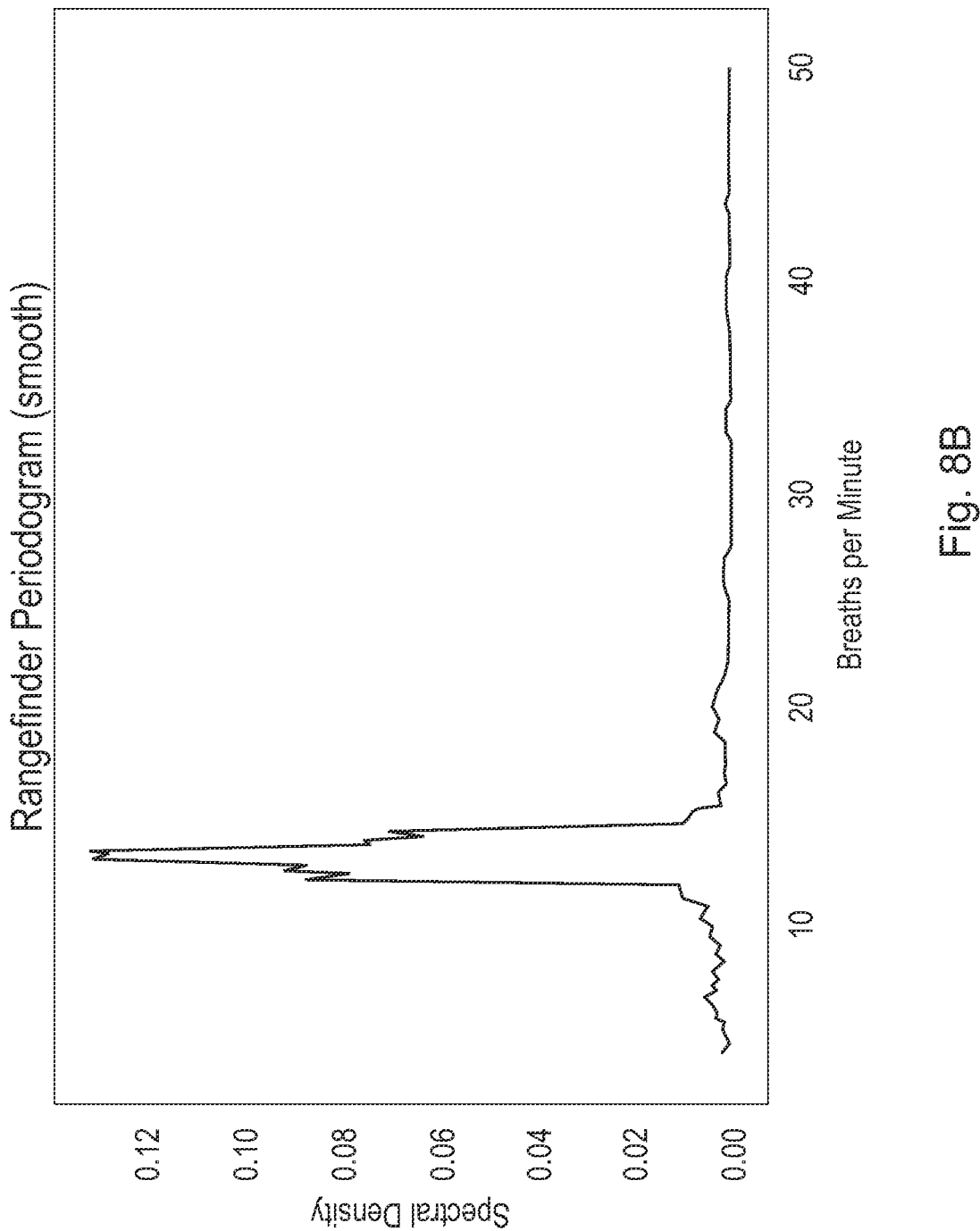
FIG. 8B is an example smoothed periodogram based on data captured by a rangefinder, in accordance with an example.

Once the four periodograms 108 are generated, a weighted average calculator 119 generates an averaged periodogram 110. The weighted average calculator 119 determines a weighted average of all four periodograms 108 based on weights 128 corresponding to eigenvalues 126 of the series of four DPSS window functions 104. FIG. 7A illustrates an averaged periodogram 110 generated based on an output sensor signal 202 from an RGB camera. FIG. 7B illustrates an averaged periodogram 110 generated based on an output sensor signal 202 from a laser rangefinder. In some examples, the averaged periodogram 110 is processed by a smoothing algorithm, such as a Thomson multitaper smoothing algorithm. FIG. 8A illustrates a smoothed version of the averaged periodogram 110 (generated based on RGB camera data) of FIG. 7A. FIG. 8B illustrates a smoothed version of the averaged periodogram 110 (generated based on laser rangefinder data) of FIG. 7B.

The averaged periodogram 110 (smoothed or raw) is then provided to a frequency analyzer 121 to determine breaths per minute data 116 based on the averaged periodogram 110. In particular, the frequency analyzer 121 determines a respiration frequency 112 corresponding to the peak estimate spectral density 114 of the averaged periodogram 110. The frequency analyzer outputs this frequency 112 as breaths per minute data 116. For example, in FIGS. 7A-8B, the respiration rate is estimated to be approximately 13 breaths per minute. The breaths per minute data 116 is then transmitted, via wired or wireless connection, to the display 500 to be shown on a display screen.

Figure 3:
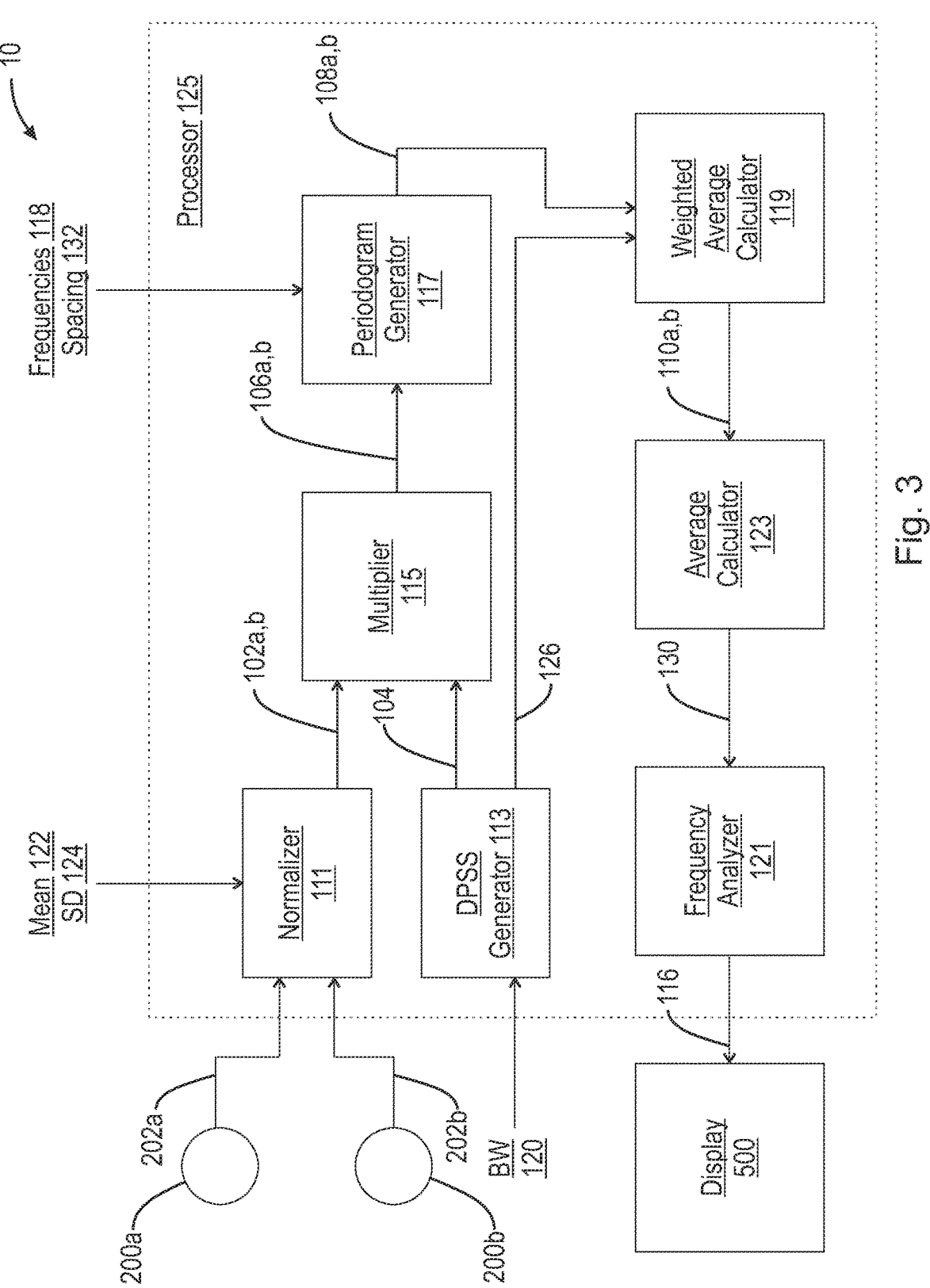
FIG. 3 is a block diagram of a multi-sensor system for long-distance respiration rate measurement, in accordance with an example.
Figure 9:
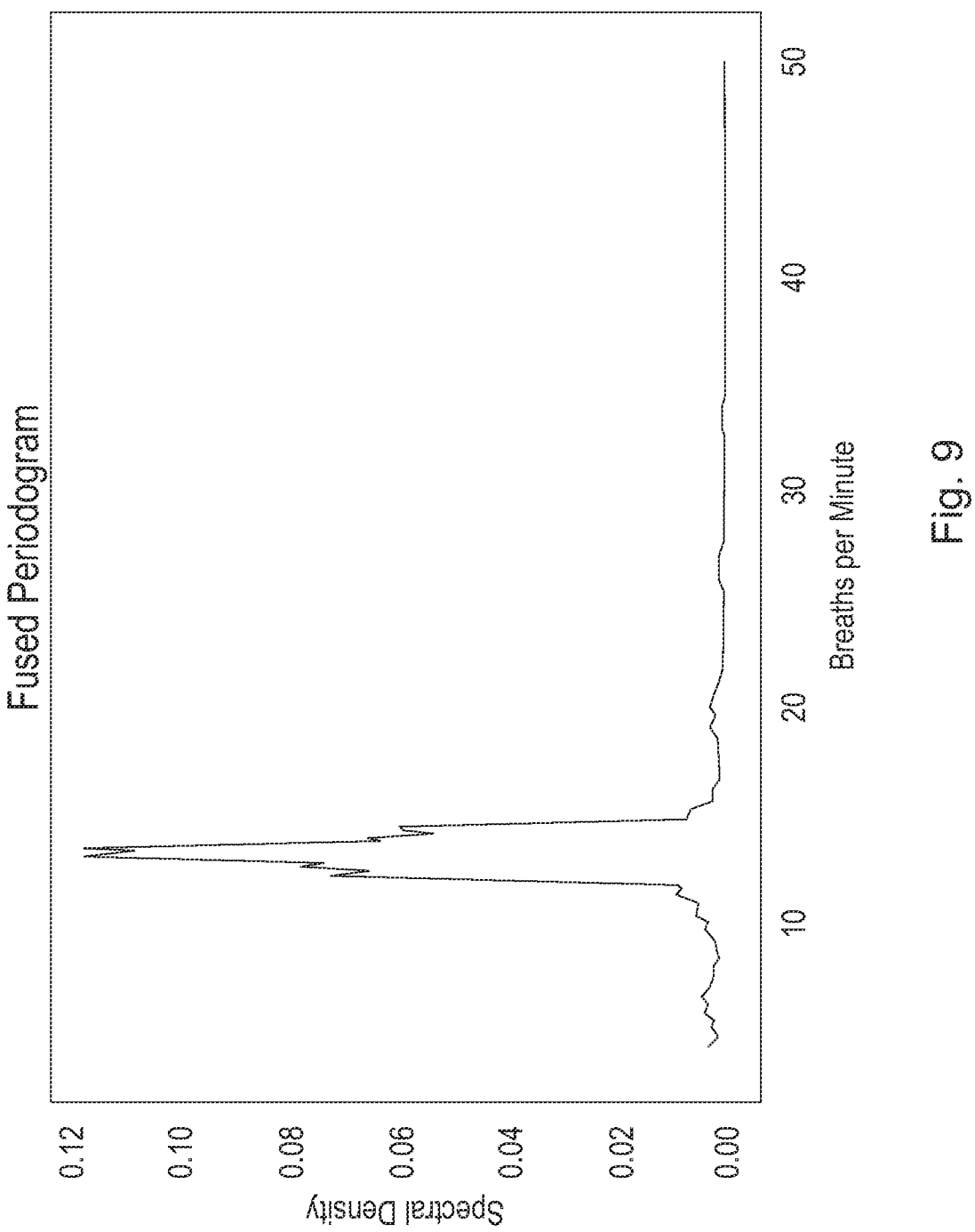
FIG. 9 is an example fused periodogram based on data captured by both a camera and a rangefinder, in accordance with an example.

FIG. 3 shows a variation of the block diagram of FIG. 2 involving the processing of two output sensor signals 202a, 202b from two sensors 200a, 200b. For example, the first sensor 200a may be an RGB camera, while the second sensor 200b may be a laser rangefinder. The normalizer 111 normalizes the output sensor signals 202a, 202b, resulting in two normalized output sensor signals 102a, 102b. Both of the normalized output sensor signals 102a, 102b are then multiplied by each of the four DPSS window functions 104, resulting in two sets of four windowed output signals 106a, 106b. The windowed output signals 106a, 106b are then processed to generate two sets of four Lomb-Scargle periodograms 108a, 108b. Each set 108a, 108b is averaged to generate two averaged periodograms 110a, 110b; a first averaged periodogram 110a (see FIG. 7A) corresponding to the first sensor 200a (such as an RGB camera) and a second averaged periodogram 110b (see FIG. 7B) corresponding to the second sensor 200b (such as a laser rangefinder). The two averaged periodograms 110a, 110b are then averaged together by an average calculator 123 to generate a multi-input averaged ("fused") periodogram 130. An example multi-input averaged periodogram is shown in FIG. 9. This multi-input averaged periodogram 108 is then analyzed to estimate respiration rate.

Figure 10:
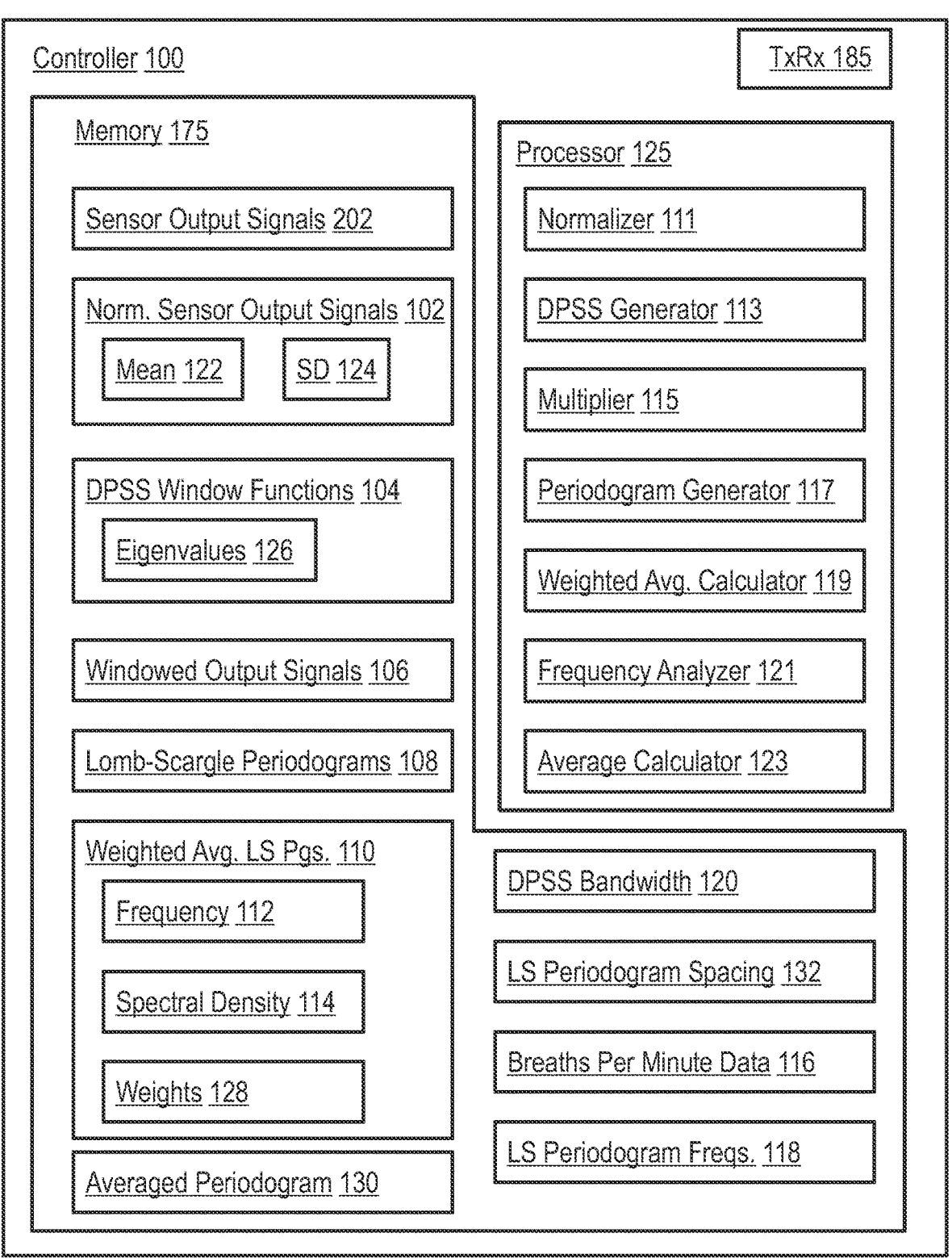
FIG. 10 is a schematic diagram of a controller of a system for long-distance respiration rate measurement, in accordance with an example.

FIG. 10 schematically illustrates the controller 100 previously depicted in FIG. 1. The controller 100 includes the processor 125, the memory 175, and the transceiver 185. The processor 125 is configured to execute the normalizer 111, the DPSS generator 113, the multiplier 115, the Lomb-Scargle periodogram generator 117, the weighted average calculator 119, the frequency analyzer 121, and the average calculator 123. The memory 175 is configured to store the sensor output signals 202, the normalized sensor output signals 102 (normalized according to stored mean 122 and standard deviation 124), the DPSS window functions 104 (and corresponding eigenvalues 126), the windowed output signals 106, the Lomb-Scargle periodograms 108, the weighted average Lomb-Scargle periodograms 110 (including frequency 112 corresponding to peak spectral density 114 and weights 128), the breaths per minute data 116, the Lomb-Scargle frequencies 118, the DPSS bandwidth 120, the multi-input averaged periodogram 130, and the Lomb-Scargle periodogram spacing 132.

Figure 11:
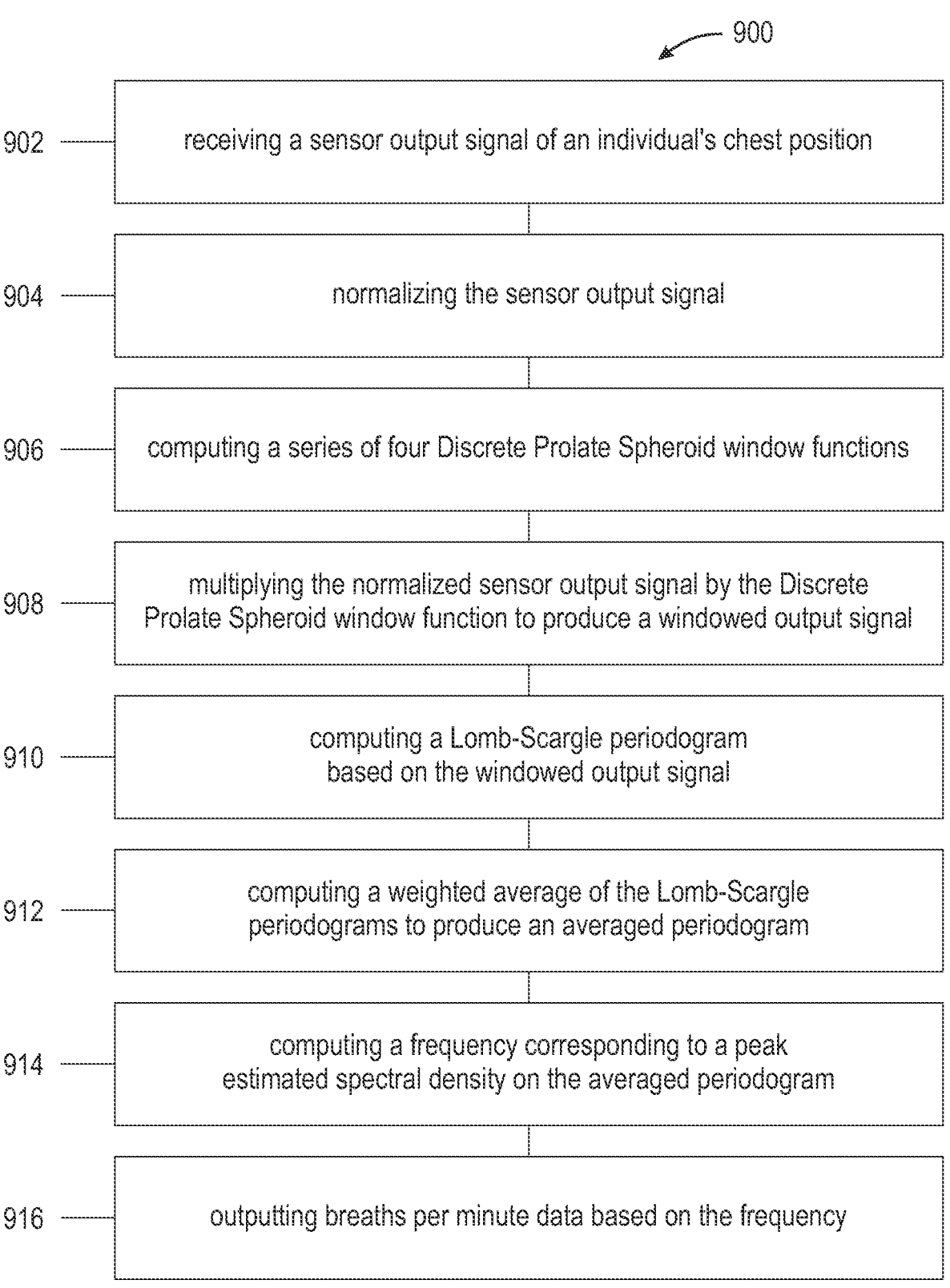
FIG. 11 is a flow chart of a method for long-distance respiration rate measurement, in accordance with an example.
Figure 12:
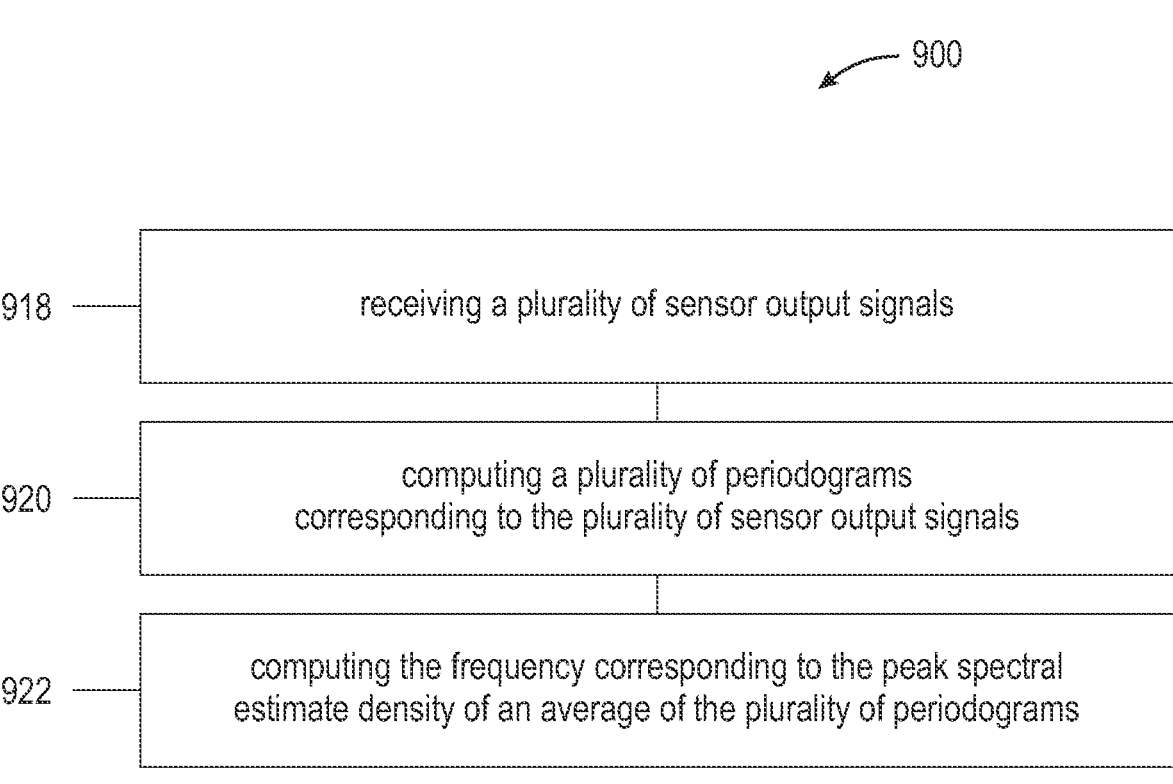
FIG. 12 is a further flow chart of aspects of a method for long-distance respiration rate measurement, in accordance with an example.

FIGS. 11 and 12 are flow charts of a method 900 for measuring long-distance respiration rate. Referring to FIGS. 1-12, the method 900 includes, in step 902, receiving a sensor output signal 202 of an individual's chest position CP.

The method 900 further includes, in step 904, normalizing the sensor output signal 202.

The method 900 further includes, in step 906, computing a series of four Discrete Prolate Spheroid window functions 104. For each of the series of four Discrete Prolate Spheroid window functions 104, the method 900 further includes, in step 908 multiplying the normalized sensor output signal 102 by the Discrete Prolate Spheroid window function 104 to produce a windowed output signal 106, and, in step 910, computing a Lomb-Scargle periodogram 108 based on the windowed output signal 106.

The method 900 further includes, in step 912, computing a weighted average of the Lomb-Scargle periodograms 108 to produce an averaged periodogram 110.

The method 900 further includes, in step 914, computing a frequency 112 corresponding to a peak estimated spectral density 114 on the averaged periodogram 110.

The method 900 further includes, in step 916, outputting breaths per minute data 116 based on the frequency 112.

According to an example, each of the series of the Discrete Prolate Spheroid window functions 104 is computed using a bandwidth 120 of 8 seconds. Further, eigenvalues 126 of the series of four Discrete Prolate Spheroid window functions 104 may be used as weights 128 to compute the weighted average.

According to an example, the Lomb-Scargle periodogram 108 is computed using a sequence of frequencies 118 ranging from 4 to 50 breaths per minute. Further, the Lomb-Scargle periodogram 108 may be spaced at 0.01 breaths per minute.

According to an example, and as shown in FIG. 12, the method 900 may further include (1) in optional step 918, receiving a plurality of sensor output signals 202, (2) in optional step 920, computing a plurality of periodograms 110 corresponding to the plurality of sensor output signals 202; and (3) in optional step 922, computing the frequency 112 corresponding to the peak spectral estimate density 114 of an average of the plurality of periodograms 110.

According to an example, the sensor output signal 202 is normalized to have a mean 122 of 0 and a standard deviation 124 of 1.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The above-described examples of the described subject matter can be implemented in any of numerous ways. For example, some aspects may be implemented using hardware, software, or a combination thereof. When any aspect is implemented at least in part in software, the software code can be executed on any suitable processor or collection of processors, whether provided in a single device or computer or distributed among multiple devices/computers.

The present disclosure may be implemented as a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of instructions, which comprises one or more executable instructions for implementing the specified logical function 13
14

(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other implementations are within the scope of the following claims and other claims to which the applicant may be entitled.

While various examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific examples described herein. It is, therefore, to be understood that the foregoing examples are presented by way of example only and that, within the scope of the appended claims and equivalents thereto, examples may be practiced otherwise than as specifically described and claimed. Examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A system for measuring long-distance respiration rate, the system comprising:
   a processing unit configured to:
      receive a sensor output signal;
      normalize the sensor output signal;
      compute a series of four Discrete Prolate Spheroid window functions, and for each of the series of four Discrete Prolate Spheroid window functions:
         multiply the normalized sensor output signal by the Discrete Prolate Spheroid window function to produce a windowed output signal, and
         compute a Lomb-Scargle periodogram based on the windowed output signal;
      compute a weighted average of the Lomb-Scargle periodograms to produce an averaged periodogram;
      compute a frequency corresponding to a peak estimated spectral density on the averaged periodogram; and
      output breaths per minute data based on the frequency.

2. The system of claim 1, further comprising:
   a plurality of sensors configured to measure a chest position (CP) of an individual (I) and provide a plurality of sensor output signals; and
   wherein the processing unit is further configured to:
      compute a plurality of periodograms corresponding to the plurality of sensor output signals, and
      compute the frequency corresponding to the peak spectral estimate density of an average of the plurality of periodograms.

3. The system of claim 1, wherein the Lomb-Scargle periodogram is computed using a sequence of frequencies ranging from 4 to 50 breaths per minute.

4. The system of claim 1, wherein the Lomb-Scargle periodogram is spaced at 0.01 breaths per minute.

5. The system of claim 1, wherein each of the series of the Discrete Prolate Spheroid window functions is computed using a bandwidth of 8 seconds.

6. The system of claim 1, further comprising a display unit configured to receive and display the breaths per minute data.

7. The system of claim 1, wherein the processing unit is configured to normalize the sensor output signal to have a mean of 0 and a standard deviation of 1.

8. The system of claim 1 wherein eigenvalues of the series of four Discrete Prolate Spheroid window functions are used as weights to compute the averaged periodogram.

9. The system of claim 1 further comprising:
   a sensor configured to measure a chest position (CP) of an individual (I) and provide the sensor output signal based on the chest position (CP) of the individual (I);
   wherein the sensor is an RGB camera or a laser rangefinder.

10. A method of measuring long-distance respiration rate, the method comprising:
   receiving a sensor output signal of an individual's chest position;
   normalizing the sensor output signal;
   computing a series of four Discrete Prolate Spheroid window functions, and for each of the series of four Discrete Prolate Spheroid window functions:
      multiplying the normalized sensor output signal by the Discrete Prolate Spheroid window function to produce a windowed output signal,
      computing a Lomb-Scargle periodogram based on the windowed output signal;
   computing a weighted average of the Lomb-Scargle periodograms to produce an averaged periodogram;
   computing a frequency corresponding to a peak estimated spectral density on the averaged periodogram; and
   outputting breaths per minute data based on the frequency.

11. The method of claim 10, wherein each of the series of the Discrete Prolate Spheroid window functions is computed using a bandwidth of 8 seconds, and eigenvalues of the series of four Discrete Prolate Spheroid window functions are used as weights to compute the weighted average.

12. The method of claim 10, wherein the Lomb-Scargle periodogram is computed using a sequence of frequencies ranging from 4 to 50 breaths per minute, and wherein the Lomb-Scargle periodogram is spaced at 0.01 breaths per minute.

13. The method of claim 10 further comprising:
   receiving a plurality of sensor output signals;
   computing a plurality of periodograms corresponding to the plurality of sensor output signals; and
   computing the frequency corresponding to the peak spectral estimate density of an average of the plurality of periodograms.

14. The method of claim 10, wherein the sensor output signal is normalized to have a mean of 0 and a standard deviation of 1.

15. A non-transitory computer readable storage medium embodied thereon a program executable by a processor for performing a method for measuring long distance respiration rate, the method comprising:

receiving a sensor output signal of an individual's chest position;

normalizing the sensor output signal;

computing a series of four Discrete Prolate Spheroid window functions, and for each of the series of four Discrete Prolate Spheroid window functions:

multiplying the normalized sensor output signal by the Discrete Prolate Spheroid window function to produce a windowed output signal, computing a Lomb-Scargle periodogram based on the windowed output signal;

computing a weighted average of the Lomb-Scargle periodograms to produce an averaged periodogram;

computing a frequency corresponding to a peak estimated spectral density on the averaged periodogram; and outputting breaths per minute data based on the frequency.

\* \* \* \* \*